(12) United States Patent
Emery

(10) Patent No.: US 11,020,834 B2
(45) Date of Patent: Jun. 1, 2021

(54) SYSTEMS AND METHODS FOR SORTING INSECTS

(71) Applicant: BETA HATCH INC., Leavenworth, WA (US)

(72) Inventor: Virginia Emery, Leavenworth, WA (US)

(73) Assignee: BETA HATCH INC., Leavenworth, WA (US)

( * ) Notice: Subject to any disclaimer, the term of this patent is extended or adjusted under 35 U.S.C. 154(b) by 0 days.

(21) Appl. No.: 16/759,268

(22) PCT Filed: Oct. 29, 2018

(86) PCT No.: PCT/US2018/058029
§ 371 (c)(1),
(2) Date: Apr. 24, 2020

(87) PCT Pub. No.: WO2019/084554
PCT Pub. Date: May 2, 2019

(65) Prior Publication Data
US 2020/0375161 A1   Dec. 3, 2020

Related U.S. Application Data

(60) Provisional application No. 62/578,029, filed on Oct. 27, 2017.

(51) Int. Cl.
*B23Q 7/12* (2006.01)
*B23Q 7/00* (2006.01)
(Continued)

(52) U.S. Cl.
CPC ............... *B23Q 7/12* (2013.01); *B23Q 7/003* (2013.01); *B23Q 7/02* (2013.01); *B23Q 7/03* (2013.01); *B65G 37/00* (2013.01)

(58) Field of Classification Search
CPC .......... B23Q 7/003; B23Q 7/03; B23Q 7/035; B23Q 7/12; B07B 1/22; B07B 1/24;
(Continued)

(56) References Cited

U.S. PATENT DOCUMENTS 3,942,644 A * 3/1976 Vissers ................... B22C 5/085
                                                     209/683
3,965,509 A   6/1976 Barber
(Continued)

FOREIGN PATENT DOCUMENTS

| CN | 103168762 B | 2/2015 |
| KR | 101464734 B1 | 11/2014 |
| WO | 2018229004 A1 | 12/2018 |

OTHER PUBLICATIONS

International Search Report and Written Opinion, dated Feb. 21, 2019, issued in priority International Application No. PCT/US2018/058029, filed Oct. 29, 2018, 10 pages.
(Continued)

*Primary Examiner* — Tyrone V Hall, Jr.
(74) *Attorney, Agent, or Firm* — Christensen O'Connor Johnson Kindness PLLC

(57) ABSTRACT

Disclosed herein is an insect sorting system that includes a conveyor stage having a drive unit, a grasping surface movably coupled with the drive unit and having textured surface elements, and a diverter that is configured to remove insects from the grasping surface.

11 Claims, 13 Drawing Sheets

(51) Int. Cl.
*B23Q 7/02* (2006.01)
*B23Q 7/03* (2006.01)
*B65G 37/00* (2006.01)

(58) Field of Classification Search
CPC .... B07B 4/00; B07B 4/06; B07B 7/00; B07B 7/01; B07B 7/12; A01M 5/00; A01M 5/02; A01M 5/04; A01M 5/06; B65G 37/00
See application file for complete search history.

(56) References Cited

U.S. PATENT DOCUMENTS

| | | | |
|---|---|---|---|
| 4,040,810 A | 8/1977 | Eby et al. | |
| 4,114,762 A * | 9/1978 | Beal | A01M 5/00 209/615 |
| 4,115,257 A * | 9/1978 | Mugler | B07B 1/22 209/267 |
| 4,293,966 A | 10/1981 | Weiderrich | |
| 5,660,340 A * | 8/1997 | Baughman | A23B 4/07 241/172 |
| 5,759,224 A | 6/1998 | Olivier | |
| 10,086,406 B2 * | 10/2018 | Charreyre | B07B 1/24 |
| 10,112,215 B1 * | 10/2018 | Coots | B07B 1/22 |
| 2018/0065152 A1 | 3/2018 | Hasa et al. | |

OTHER PUBLICATIONS

Third Party Observation and Additional Comments Submitted with Observation, mailed Feb. 26, 2020, issued in priority International Application No. PCT/US2018/058029, filed Oct. 29, 2018, 11 pages.

* cited by examiner

SYSTEMS AND METHODS FOR SORTING INSECTS

CROSS-REFERENCE TO RELATED APPLICATIONS

This application is a national phase application of International Patent Application No. PCT/US2018/058029, filed on Oct. 29, 2018, which claims the benefit of provisional application Ser. No. 62/578,029, filed on Oct. 27, 2017, and titled "Machine For Sorting Crawling Insects," each of which is hereby incorporated by reference in its entirety.

BACKGROUND

Insects have been widely considered as pests, and human efforts are directed to reduce the number of pest from living environments. However, insects are also known to contain nutrition, including protein and fats, and thus are a nutritious food source. For this reason, insects are now used as a food source for livestock, such as chicken and other types of birds.

To provide the best nutrition, insect larvae may be raised until before they become pupae and harvested for livestock feed. Although insects, such as mealworms, are easier to raise than some other species (e.g., livestock), there are some challenges. One challenge is sorting insects into active (live) or inactive (dead) categories. Another challenge is sorting larvae from non-larvae. Efficient sorting is necessary to efficiently raise insects on a large scale. Conventional sorting methods involve a high degree of manual labor, which is expensive and slow.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In an aspect, an insect sorting system is provided that includes a conveyor stage having a drive unit, a grasping surface movably coupled with the drive unit and having textured surface elements, and a diverter that is configured to remove insects from the grasping surface. The diverter may be positioned within 5.0 mm from the grasping surface, and may be in contact with the grasping surface. The conveyor stage may be configured to move the grasping surface past the diverter at a rate, which may be adjustable, that is between 0.5 cm per second and 100 cm per second. The conveyor stage may include an angled tube. A trough may be positioned within the angled tube, at least part of the trough being positioned gravitationally below the diverter. The diverter may be contiguous with the trough. The grasping surface may be located within the angled tube. The angled tube may be substantially formed by the grasping surface. The diverter may be positioned external to the angled tube. A longitudinal axis of the conveyor stage may form an angle, which may be adjustable, that is between 5 degrees and 30 degrees relative to a horizontal surface. The diverter may be selected from the group consisting of: a fixed brush, a rotating brush, a wiper, a scraper, a straight edge, a gas curtain, and a liquid curtain. The grasping surface may include a mesh. The grasping surface may form at least part of a continuous loop having an upper section and a lower section, and in such embodiments, the grasping surface may face outwardly from the continuous loop. In an embodiment with a continuous loop having an upper section and a lower section, the diverter may be positioned adjacent to the lower section of the continuous loop. In all embodiments, the conveyor stage may be a first conveyor stage and the system may further include a second conveyor stage. In an embodiment with a first and a second conveyor stage, at least a portion of the second conveyor stage may be positioned gravitationally below the first conveyor stage and may be configured to receive a portion of an insect supply via the first conveyor stage. The first and second conveyor stages are configured to receive a portion of an insect supply directly from a hopper. The grasping surface of the first conveyor stage may be a first grasping surface having a first roughness, wherein the second conveyor stage may have a second grasping surface having a second roughness. The insect sorting system may include a hopper an outlet, and at least a portion of the conveyor stage may be located gravitationally below the outlet. The insect sorting system may include a collector located gravitationally below the diverter.

In another aspect, a method of sorting insects includes: providing an insect supply onto a grasping surface having textured surface elements; separating an active portion of the insect supply from an inactive portion of the insect supply by removing the active portion from the grasping surface with a diverter; and allowing the inactive portion to fall off the grasping surface.

BRIEF DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

Figure 1:
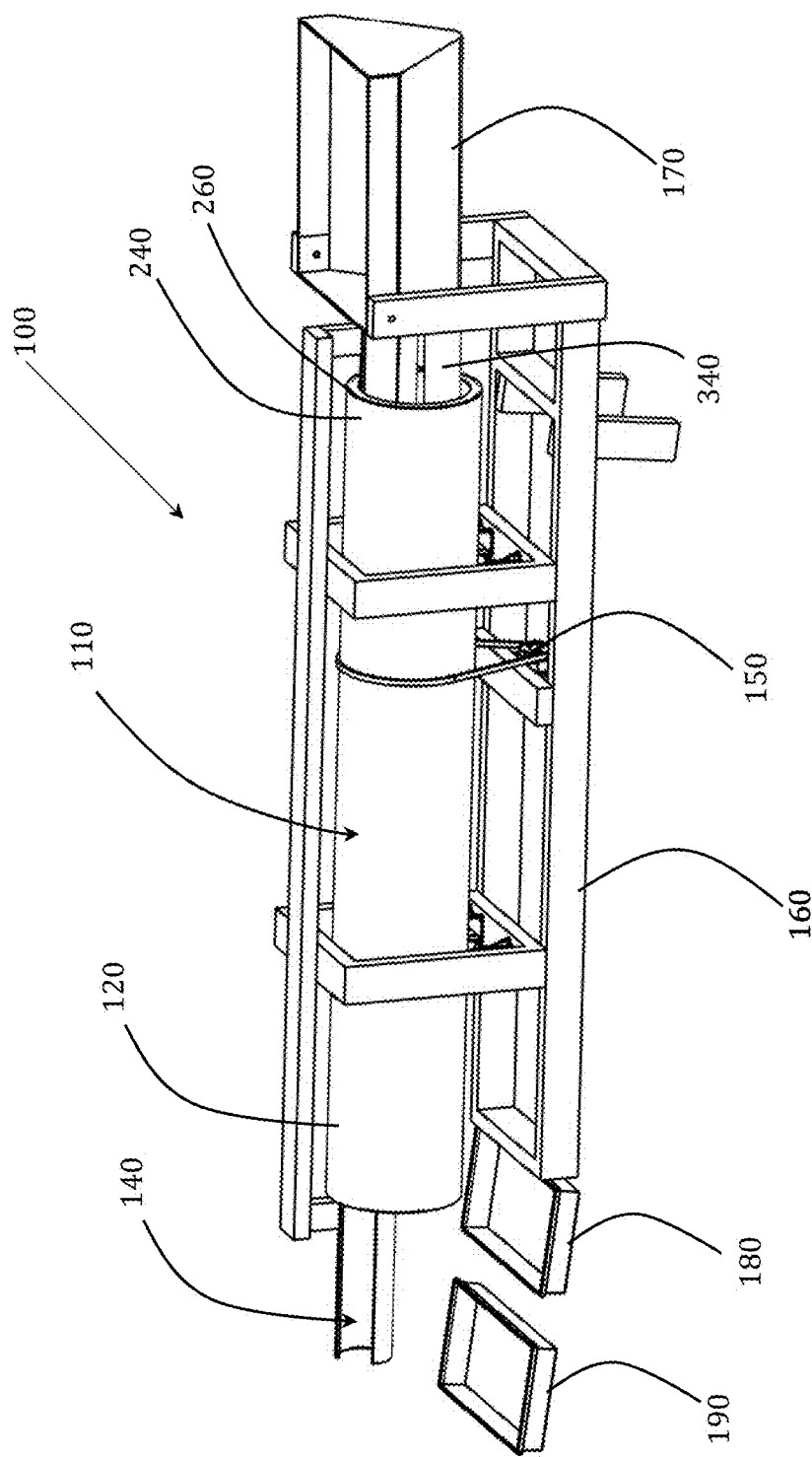
FIG. 1 is a perspective view of a representative insect sorting system according to an embodiment of the present disclosure.

An appendix is included herewith to provide additional details of the insect sorting systems of the present disclosure.

DETAILED DESCRIPTION

By way of overview, the present disclosure is directed to systems and methods for efficiently sorting insects, especially sorting live insects (active insects) from dead or non-larval insects (inactive insects), or sorting adult insects from immature insects. In general, insect sorting systems of the present disclosure may include one or more conveyor stages for separating active insects from inactive insects. The conveyor stage generally has one or more grasping surfaces with textured surface elements configured to permit live insects (in particular larval insects) to grasp the surface such that the live insect generally stays with the grasping surface even when the grasping surface moves (e.g., is inclined, rotated, or inverted). In one embodiment the textured surface elements are raised surface elements. Generally, the grasping surface has sufficient texture for insects' prolegs—or for adult insects, tarsi—to grab. By taking advantage of live insects' (e.g., larvae) nature to grasp onto surfaces, especially surfaces with mesh materials, live insects (e.g., larvae) can be isolated from non-larval insects, such as pupae, or dead insects, both of which naturally lack the ability to grasp on such surfaces. Suitable grasping surfaces may include mesh materials. For example, a larger mesh may effectively be used to separate live and dead adult insects because the adults can more actively grab the grasping surface. Also, because of the more balanced position of the legs of adult insects (as compared to immature insects), they are able to grab with six points of contact which distribute their weight more evenly. By comparison, larvae have prolegs only at the front end of the body and are less balanced when grasping the textured grasping surface, and therefore may require a more textured surface area (e.g., a smaller mesh) to grasp firmly. Thus, when a mixture of insects are introduced onto the conveyor stage having a grasping surface, live insects can grasp the grasping surface, while dead or non-larval do not grasp the grasping surface. The grasping surface can be moved such that the live insects "stick" to the moving grasping surface, and dead or inactive insects do not. The active insects can then be harvested from one part of the grasping surface, and the inactive insects may be removed from another part of the grasping surface with the aid of gravity (e.g., by falling off of the grasping surface). The active and inactive insects may then be collected in separate collectors.

The conveyor stage may include one or more angled tubes and/or one or more continuous loops. The systems may optionally include one or more hoppers for supplying insects to the one or more conveyor stages, and one or more collectors for collecting insects from a conveyor stage. Suitable hoppers may include mechanisms to regulate the dispensation of insects, such as a volumetric screw auger, a weighted vibrational dispenser, a conveyor system, or other dispenser device. The insect sorting systems are modular in that a single system may include more than one conveyor stage. For example, in an embodiment, an insect sorting system may include more than one conveyor stage that is provided insects directly from the same hopper, i.e., in parallel. Additionally or alternatively, an insect sorting system may include more than one conveyor stage in series, i.e., a first conveyor stage provides insects to a second conveyor stage.

Referring to FIGS. 1-4, an insect sorting system 100 includes a conveyor stage 110 having a tube 120 with an internal grasping surface 130 (see FIGS. 3A-3C and 4), a diverter 140 located within the tube 120, and a drive unit 150 operably coupled to rotate the tube 120. A frame 160 supports at least some elements of the system 100, including components of the conveyor stage 110 such as the tube 120 and the drive unit 150. The insect sorting system 100 further includes an optional hopper 170 for loading insects, and one or more optional collectors 180 and 190. The system 100 is sized such that it can be placed on a table to facilitate insect sorting. Some embodiments may be larger or smaller.

Figure 2:
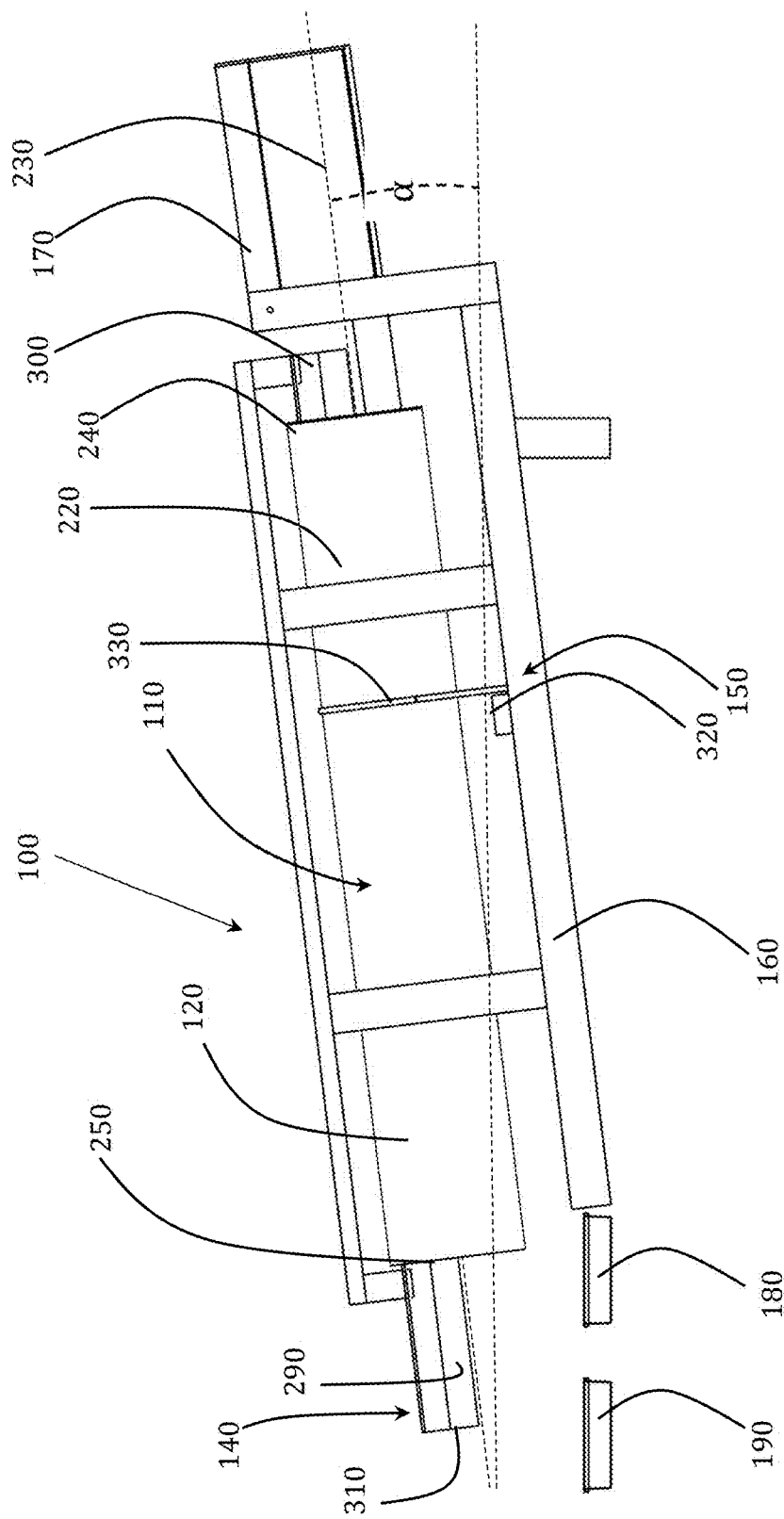
FIG. 2 is a side view of the insect sorting system of FIG. 1.
Figure 3A:
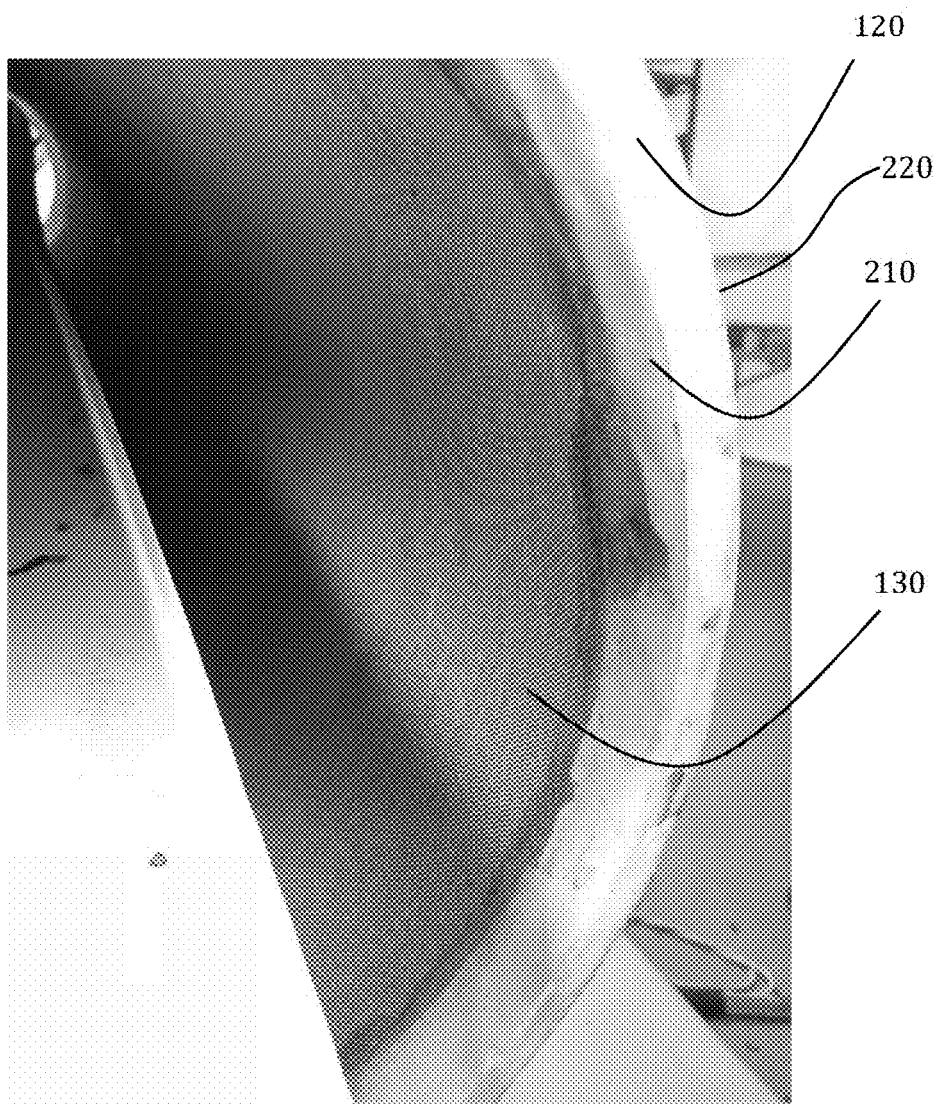
FIGS. 3A-C are perspective views of a grasping surface of the insect sorting system of FIG. 1.
Figure 4:
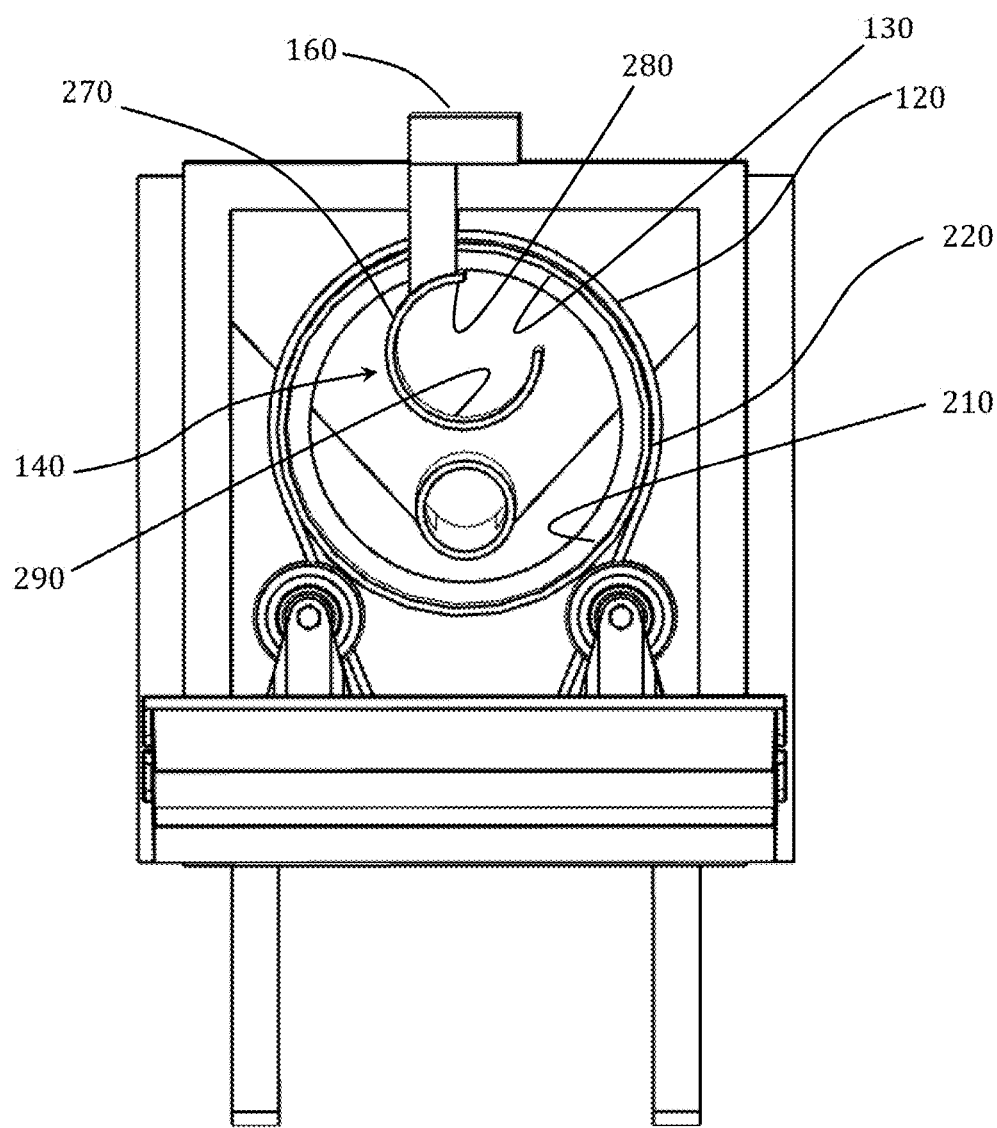
FIG. 4 is a front view of an aspect of the insect sorting system of FIG. 1.

Referring to FIGS. 3A and 4, the tube 120 has an interior surface 210 and an exterior surface 220. As shown in FIG. 2, the tube 120 has a longitudinal axis 230 and may have a length that ranges from about 10 cm to about 10 meters or greater, e.g., about 1 meter, about 1.2 meters, about 1.5 meters, about 1.8 meters, about 2 meters, and any other value in that range. The tube 120 may have an inner or outer diameter that ranges from about 10 cm to about 10 meters or greater, e.g., about 30 cm, about 60 cm, about 100 cm, or any other value in that range, depending on the application. Larger diameter tubes naturally create more surface area inside the tube, all else equal, which may advantageously improve system efficiency by providing greater surface area for insects to grasp. Suitable surface areas may range from approximately 5,000 square centimeters to about 100,000 square centimeters or more, e.g., about 10,000 square centimeters, about 20,000 square centimeters, or about any other value in that range. Some suitable and non-limiting tubes 120 may have a length of about 1.2 m and a diameter of about 30 cm; a length of about 1.8 m and a diameter of about 30 cm; a length of about 1.8 m and a diameter of about 60 cm.

With reference to FIG. 2, the longitudinal axis of the tube 120 may form an angle, $\alpha$, relative to a horizontal plane (e.g., a top of table) that ranges from about 5 degrees to about 45 degrees, including about 5 degrees to about 30 degrees, about 12 degrees to about 27 degrees, e.g., about 10 degrees, about 12 degrees, about 13 degrees, about 15 degrees, about 20 degrees, or any other value in that range. The tube 120 has an upstream end 240 and a downstream end 250. As used in this application, the term "upstream end" may refer to an end that is gravitationally higher than another end and/or an end that receives an insect supply (e.g., a supply of mealworms) first in time. Likewise, as used in this application, the term "downstream end" may refer to an end that is gravitationally lower than another end and/or an end that receives an insect supply second in time. Some embodiments may include an angle adjustment mechanism to adjust the tube angle $\alpha$. A higher angle $\alpha$ may lead to faster sorting of an insect supply; however, an angle $\alpha$ that exceeds about 45 degrees may make it difficult for active insects to grasp the grasping surface before reaching the end of the tube, which may cause active insects to fall out of the tube along with the inactive insects, thereby reducing sort efficiency.

Suitable materials for the tube 120 include metals and plastics, for example steel, aluminum, polyvinylchloride (PVC), and other rigid materials. The tube 120 may include or couple with a stopper flange 260 at the upstream end 240, which may prevent insects from crawling out of the tube 120.

The conveyor stage 110 of the illustrated embodiment includes a single tube 120. In some embodiments, the system may scale to include a plurality of conveyor stages, e.g., a plurality of tubes that are arranged in a serial, end-to-end arrangement, such that a first conveyor stage may provide an insect supply to a second conveyor stage. Additionally or alternatively, some embodiments may scale to include a parallel arrangement of conveyor stages, e.g., each conveyor stage simultaneously receives an insect supply from a common supply source (e.g., from the same hopper).

Figure 3B:
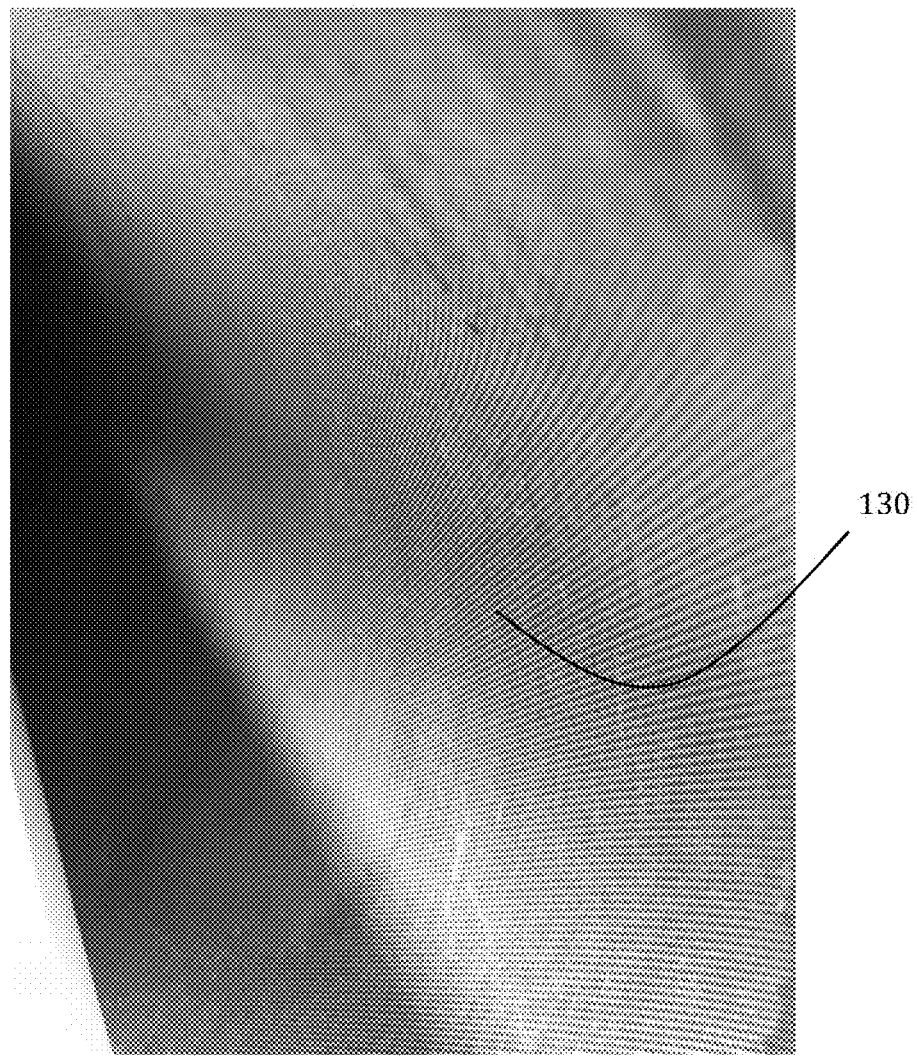
Figure 3C:
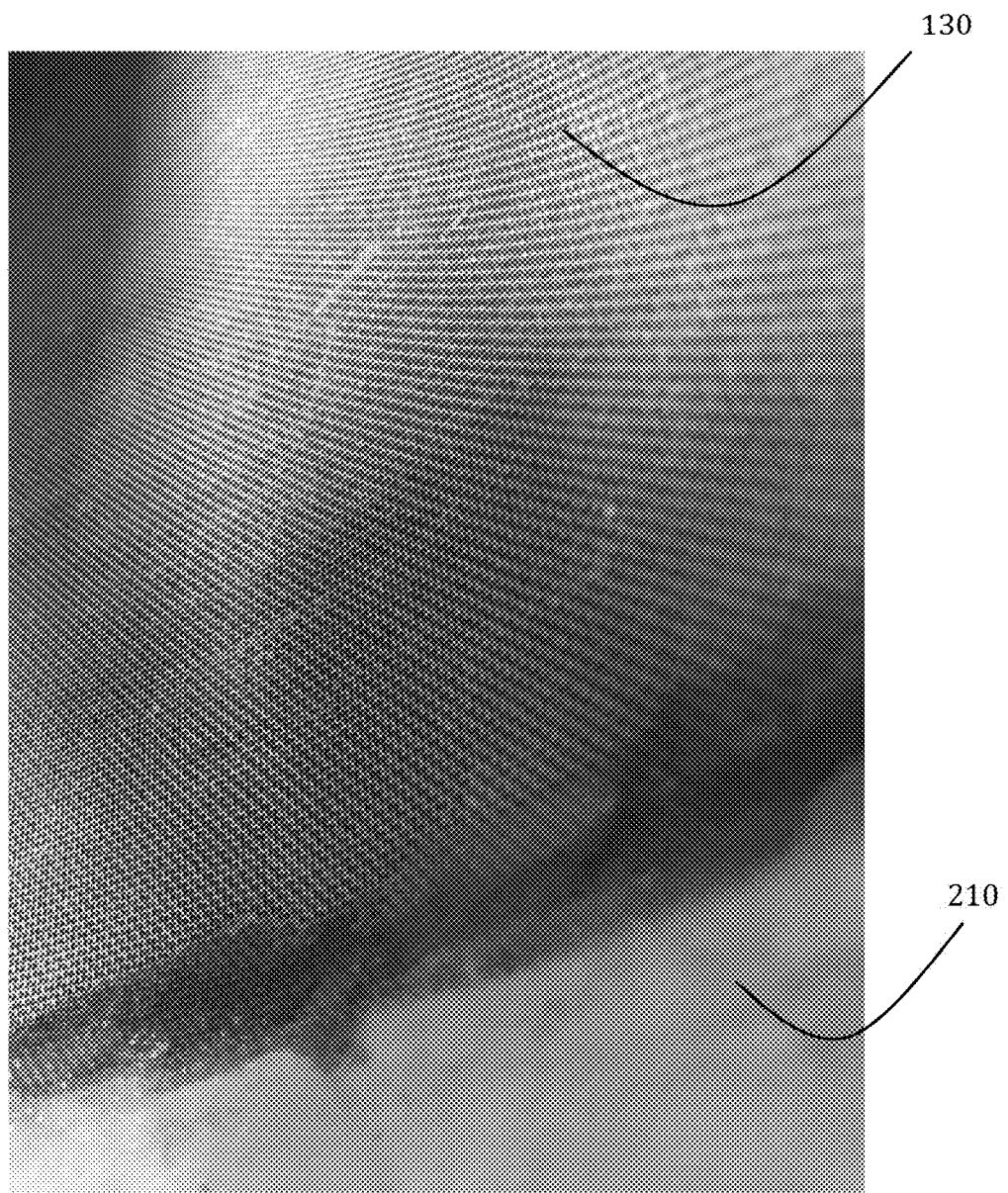

Referring to FIGS. 3A-C and to the Appendix, the grasping surface 130 faces inwardly from the interior surface 210 of the tube 120 and provides textured surface elements that active insects can grasp (e.g., live insects such as larvae). In the illustrated embodiment, the grasping surface 130 is applied to the interior surface 210 of the tube (as with an adhesive, mechanical fastener, or other means) and forms a lining to the tube 120. In some embodiments, the grasping surface may actually form part of the interior surface of the tube itself (i.e., the grasping surface may be integrally formed with the tube). When the grasping surface 130 is moved, e.g., rotated via the drive unit 150, active insects that grasp the grasping surface 130 are transported away from inactive insects that do not grasp the grasping surface 130. Generally, the grasping surface 130 has textured surface elements with dimensions that may approximate proleg and tarsal dimensions of the insects to be sorted, for example mealworms (including adult mealworms). In the illustrated embodiment, the grasping surface 130 is a mesh material, such as a fine mesh net formed of plastic and/or metallic wire, which is durable, washable, reusable, and effective. In some embodiments, the grasping surface may comprise one or more materials having textured characteristics, for example coarse meshed fabric such as canvas and burlap, fluffy fabric such as felt and flannel, and woven or knitted textiles such as woven cotton. Additionally or alternatively, other textured surfaces such as sand-coated concrete, sand-paper, plaster, paper, newspaper, and plastic film may be suitable for the grasping surface. For example, a mesh having an opening size between about 0.25 mm and about 1.0 mm, e.g., about 0.5 mm, may be suitable for separating active mealworms from non-active mealworms and from pupae. In some embodiments, a mesh having an opening size of between about 1.0 mm and about 5.0 mm, e.g., about 0.2 mm, 0.5 mm, about 1.5 mm, about 2.2 mm, or any other value in that range, may provide good results.

Some embodiments may include more than type of grasping surface, which may facilitate sorting active insects from inactive insects in an insect supply containing more than one species and/or insects of different ages, stages, and/or other different characteristic. For example, embodiments having more than one tube may include different grasping surfaces. Additionally or alternatively, a single tube may include more than one type of grasping surface.

Referring to FIG. 4, the diverter 140 is located at least partially within the tube 120 and is configured to divert or remove active insects from the grasping surface 130. In the illustrated embodiment, the diverter 140 has a scraper 270 and is supported by the frame 160. As shown in FIG. 4, the scraper 270 has an edge 280 that is positioned within about 0 cm (i.e., in direct contact) to about 1 cm from the grasping surface 130, e.g., about 0.25 cm, about 0.5 cm, about 0.75 cm, or any other value in that range. In the illustrated embodiment, the diverter 140 is integrally formed with a trough 290 such that the edge 280 of the scraper 270 is located gravitationally above the trough 290 in use. As shown in FIG. 2, the trough 290 may extend generally through the tube 120, e.g., in a direction generally aligned with the longitudinal axis of the tube, and may form an angle of about 5 degrees to about 30 degrees relative to a horizontal plane (similar to the angle α of the tube 120), such that the trough 290 forms an upstream end 300 and a downstream end 310. In some embodiments, the trough may contain a conveyor belt (not shown) that runs in the direction of the downstream end. In use, the scraper 270 removes active insects from the grasping surface 130, and the removed active insects fall from the grasping surface 130 into the trough 290. The active insects then move down the trough 290 via gravity and/or other means (e.g., an air source), such that they may ultimately fall off the trough into the collector 190.

In the illustrated embodiment, the diverter 140 is formed at least partially from metal; the diverter 140 (including the scraper 270) may alternatively be at least partially formed from one or more polymers (e.g., flexible plastic foams, silicone, high density polyethylene, or other suitable polymer), organic materials, and/or one or more metals (e.g., aluminum or steel). In some embodiments, the diverter may include additional or different structures to divert insects from the grasping surface, e.g., a fixed brush, a rotating brush, a wiper, a straight edge, a gas curtain (e.g., an air curtain that blows a puff of air at the insects to dislodge them from the grasping surface), and a liquid curtain. In some embodiments, the diverter may include a device that taps and/or hits the tube 120 to cause insects to fall off the grasping surface 130.

The drive unit 150 is operably coupled to the tube 120 such that it may move the tube 120. In particular, the drive unit 150 rotates the tube 120 on rollers such that the grasping surface 130 moves past the diverter 140 at a rate that removes active insects from the grasping surface 130 without injuring those insects. As shown in FIG. 2, the drive unit 150 includes an electric motor 320 that is coupled to the tube 120 via a pulley and a drive belt 330 extending around the exterior surface 220 of the tube 120. In some embodiments, the drive unit 150 may additionally or alternatively include components to enable manual rotation of the tube, such as a crank and a gearbox.

Generally, the grasping surface 130 may move past the diverter 140 at rates ranging from about 0.5 cm/s to about 100 cm/s, e.g., about 1 cm/s, about 10 cm/s, about 20 cm/s, about 75 cm/s, and any other value in that range. Faster rates may prevent insects from grasping the grasping surface 130; slower rates may be too inefficient. In some embodiments, the drive unit 150 may drive the grasping surface 130 intermittently, i.e., with intervals of rotation separated by intervals of no rotation. For example, the drive unit 150 may rotate the tube 120 for about 1 second to about 3 seconds, and then stop the tube's rotation for about 1 second to about 3 seconds, and then repeat the cycle. In an embodiment, the drive unit 150 alternatingly rotates the tube 120 for about three seconds following every two second pause. In some embodiments, the drive unit 150 may permit a variable rate of movement, e.g., via a controller that adjusts the motor speed, transmission, or other mechanism. In this way, the movement of the grasping surface 130 may be adjusted depending on the species and age of insect being harvested, and for the desired harvest rate. Some embodiments may include more than one drive unit 150. Some embodiments may operably connect a single drive 150 unit to more than one conveyor stage. In both types of embodiments, the different conveyor stages may be driven at different speeds.

Referring again to FIG. 1, the optional hopper 170 is configured to provide an insect supply into the conveyor stage 110. Accordingly, it has an outlet 340 that extends into the upstream end 240 of the tube 120 and is positioned gravitationally above at least part of the tube 120. The hopper 170 and/or its outlet 340 may be angled to facilitate dispensing insects into the conveyor stage 110. In the illustrated embodiment, the frame 160 supports the hopper 170, although the hopper may be free-standing in some embodiments. In some embodiments, the system may include a hopper having a plurality of outlets such that a single hopper can provide an insect supply to a plurality of conveyor stages.

In use, an insect supply containing active and inactive insects (e.g., active and inactive mealworms, such as live and dead mealworms, and/or adult and non-adult mealworms) may be introduced into the conveyor stage 110, e.g., from the hopper 170. In particular, the insect supply may be dispensed from the hopper outlet 340 into the upstream end 240 of the tube 120. The drive unit 150 may rotate the tube 120 and the grasping surface 130, e.g., clockwise or counterclockwise, when the insect supply is inside the tube 120. As the tube 120 rotates, at least some active insects will quickly become sorted from inactive insects because active insects will grasp the grasping surface 130 while inactive insects will not. For this reason, an active insect will generally remain at or around a fixed location of the grasping surface 130, even as the grasping surface 130 rotates. Thus, as that location of the grasping surface 130 moves past the diverter 140 (in particular, the scraper 270), the active insect is diverted from the grasping surface 130 and falls into the trough 290 that is located gravitationally below the scraper 270. Because the trough 290 is angled, the active insects removed from the grasping surface 130 will tend to slide or fall toward the downstream end 310 of the trough 290, and will eventually fall out of the trough 290, e.g., into the collector 190.

At the same time, the inactive insects will tend to remain in the gravitational bottom portion of the grasping surface 130 and the tube 120. Because the tube 120 is angled, the inactive insects will tend to fall toward the downstream end 250 of the tube 120, and will eventually fall out of the tube 120, e.g., into the collector 180.

Figure 5:
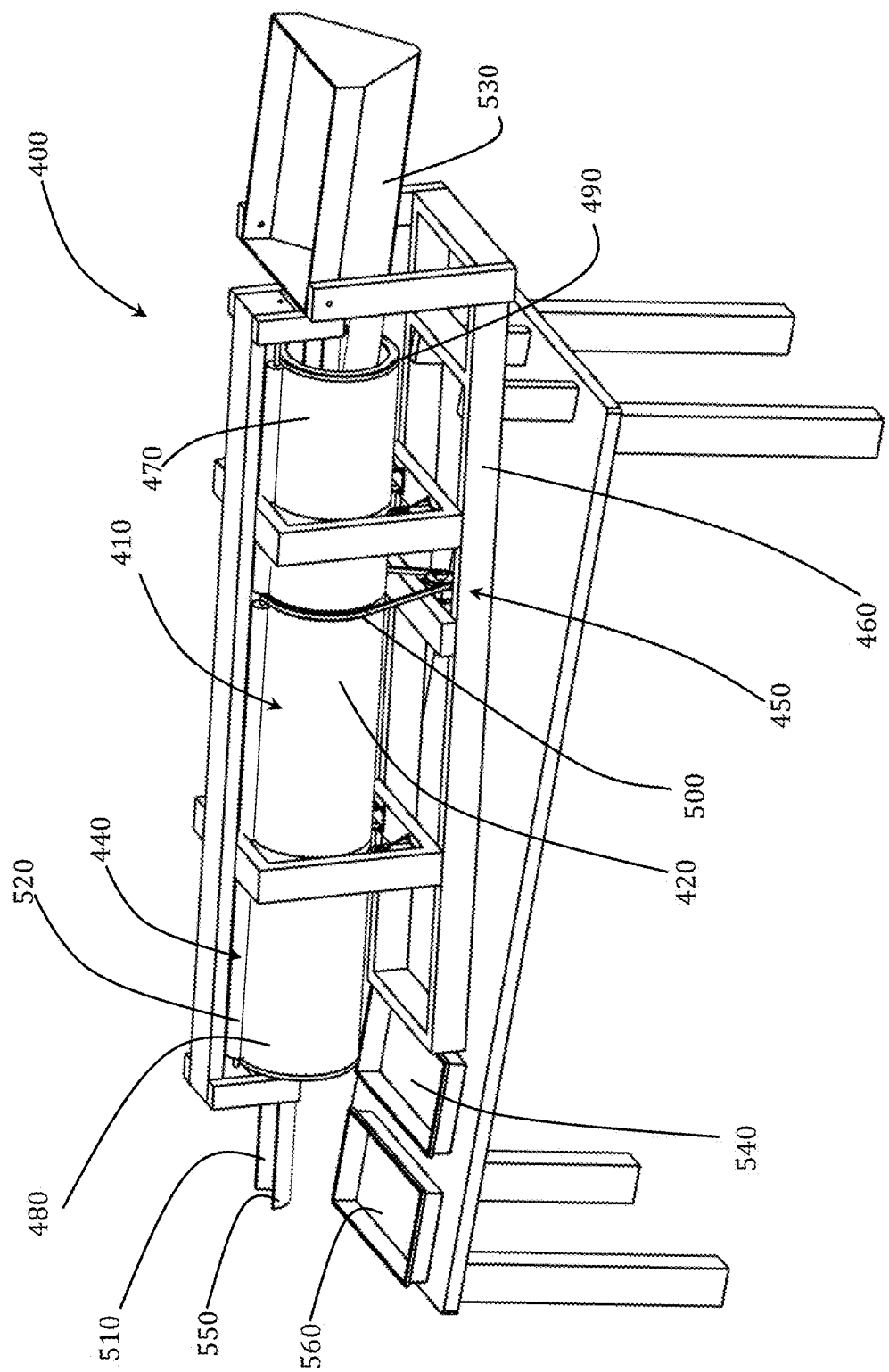
FIG. 5 is a perspective view of another representative insect sorting system according to an embodiment of the present disclosure.
Figure 6:
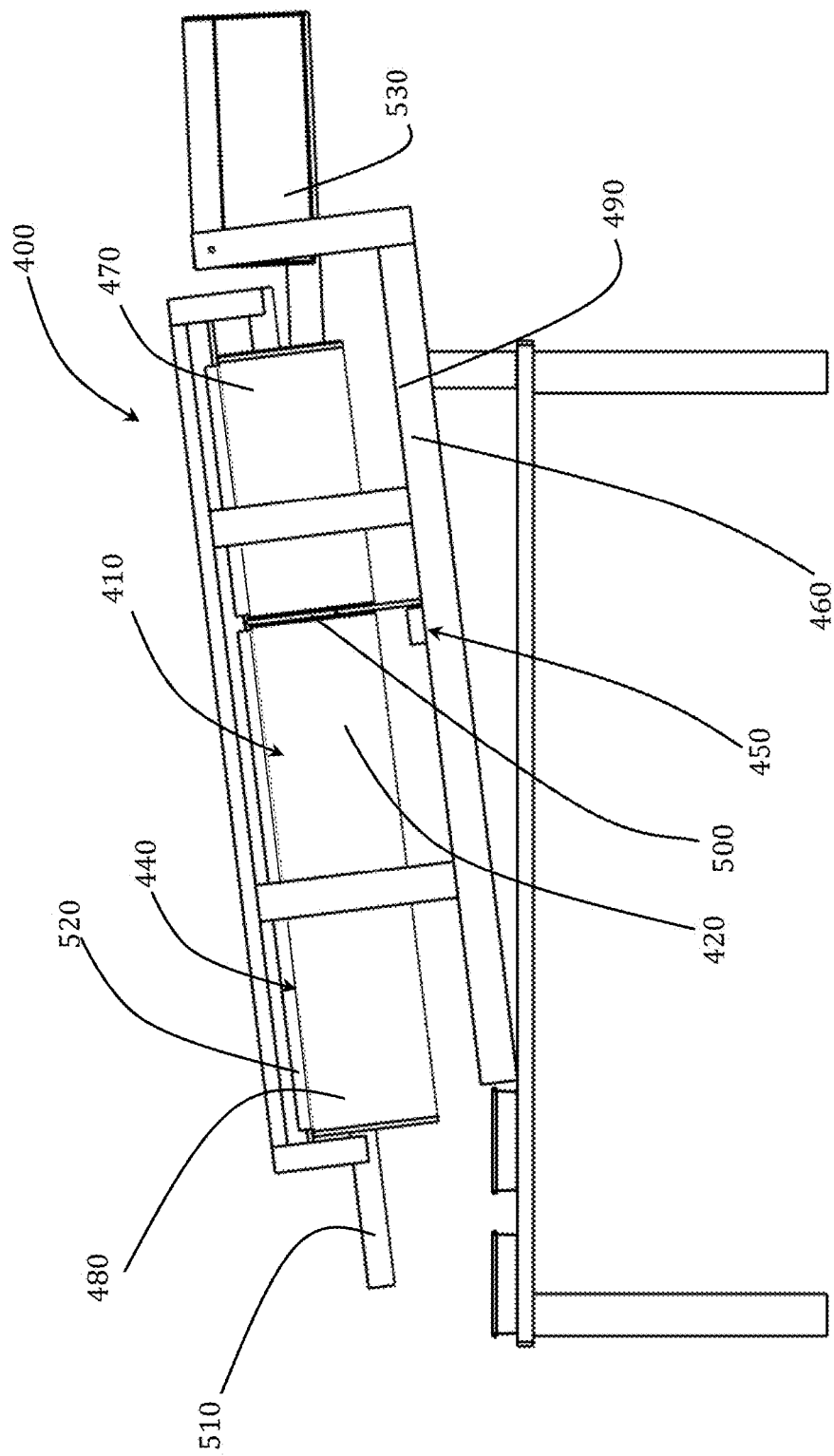
FIG. 6 is a side view of the insect sorting system of FIG. 5.
Figure 7:
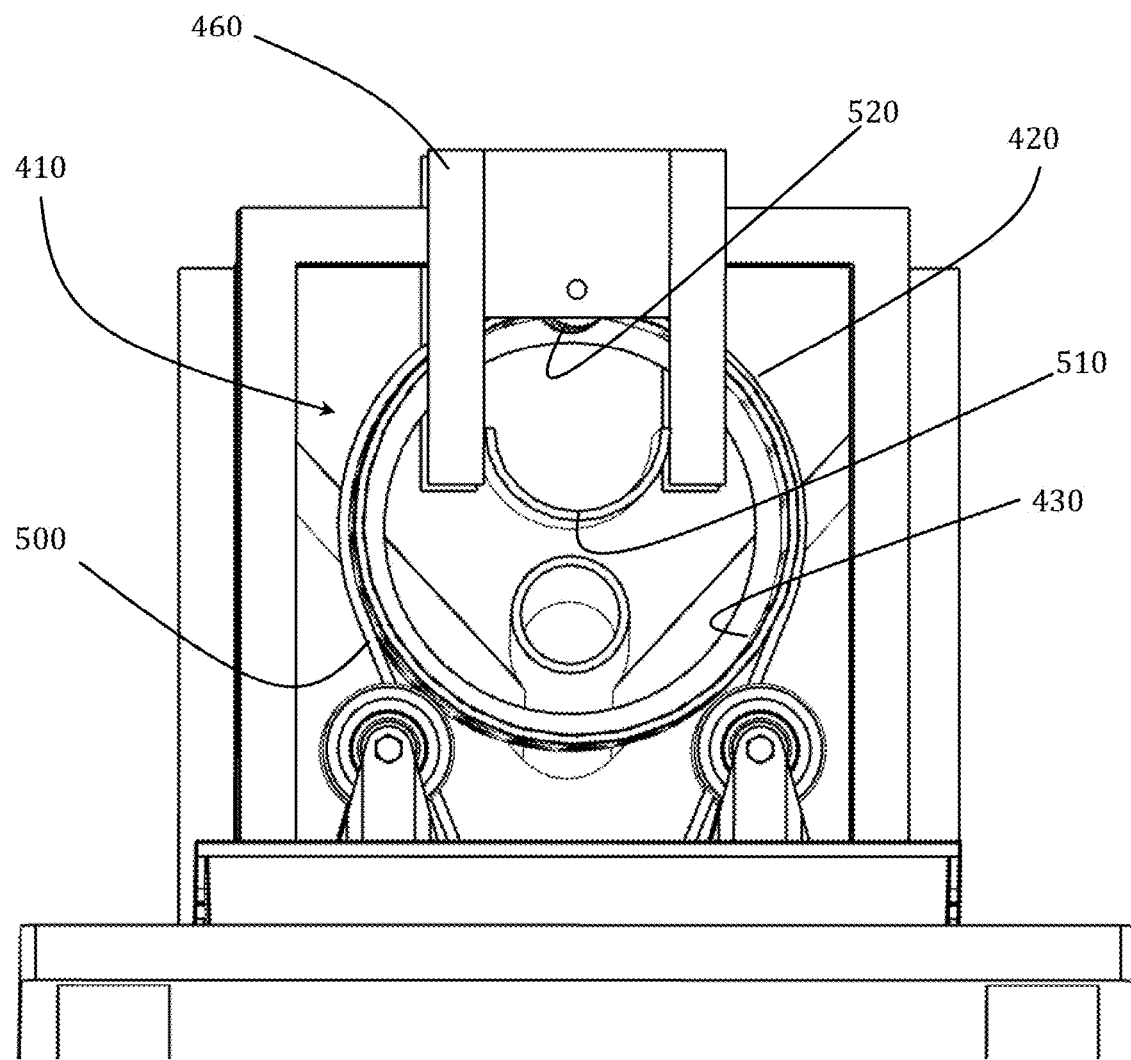
FIG. 7 is a partial front view of an aspect of the insect sorting system of FIG. 5.

FIGS. 5-7 illustrate an insect sorting system 400 that is similar in some respects to the system 100 of FIGS. 1-4. As such, the following system 400 may have any feature of the system 100 of FIGS. 1-4 except where expressly stated otherwise, and vice versa. The system 400 of FIGS. 5-7 includes a conveyor stage 410 having a tube 420 that is substantially formed by and integrally formed with a grasping surface 430 (see FIG. 7), a rotating brush-type diverter 440 located external to tube 420, and a drive unit 450 operably coupled to the tube 420 and to the diverter 440. A frame 460 supports at least some elements of the system 400, including components of the conveyor stage 410 including the tube 420, the diverter 440, and the drive unit 450. The insect sorting system further includes an optional hopper for loading insects, and one or more optional collectors. The system 400 is sized such that it can be placed on a table to facilitate insect sorting.

In the embodiment of FIGS. 5-7, the tube 420 is substantially formed of a cylindrical mesh material (e.g., with a mesh material as described above), and may include one or more support flanges (not shown) along the length of the tube 420 to maintain the cylindrical shape. The mesh material forms the grasping surface 430, and the tube 420 is substantially formed by the grasping surface 430. The mesh is fine enough so that insects do not fall through the mesh. The tube 420 may be angled relative to a horizontal plane such that it forms an upstream end 470 and a downstream end 480. A stopper flange 490 is located on the upstream end 470 of the tube 420 to prevent insects from crawling out of the system 400.

The drive unit 450 includes an electric motor coupled with a drive belt 500 that extends around an external surface of the tube 420 such that it can rotate the tube 420, e.g., in a clockwise and/or a counterclockwise direction. The conveyor stage 410 includes a trough 510 that extends through the tube 420. The trough 510 may be angled relative to horizontal and/or may include a conveyor belt (not shown).

The diverter 440 includes a rotating brush 520 that extends along the tube 420 and may be attached to the trough 510 and/or the frame 460. The rotating brush 520 has bristles that are sized to extend to or through the mesh material of the tube 420, i.e., into an interior of the tube 420 (see FIG. 7).

In use, an optional hopper 530 introduces an insect supply into the upstream end 470 of the mesh tube 420 and onto the grasping surface 430. The drive unit 450 rotates the tube 420 while the insect supply is within the tube 420. Inactive insects are carried to the downstream end 480 of the tube 420 by gravity, ultimately falling off the downstream end 480 into a first collector 540. Simultaneously, active insects grasp the rotating mesh grasping surface 430. The rotating brush 520 sweeps against an outside surface of the tube 420 such that its bristles extend through the mesh and into the tube 420, pushing the active insects off the grasping surface 430 and into the trough 510, which carries the active insects to an outlet 550, where they fall off into a collector 560.

Figure 8:
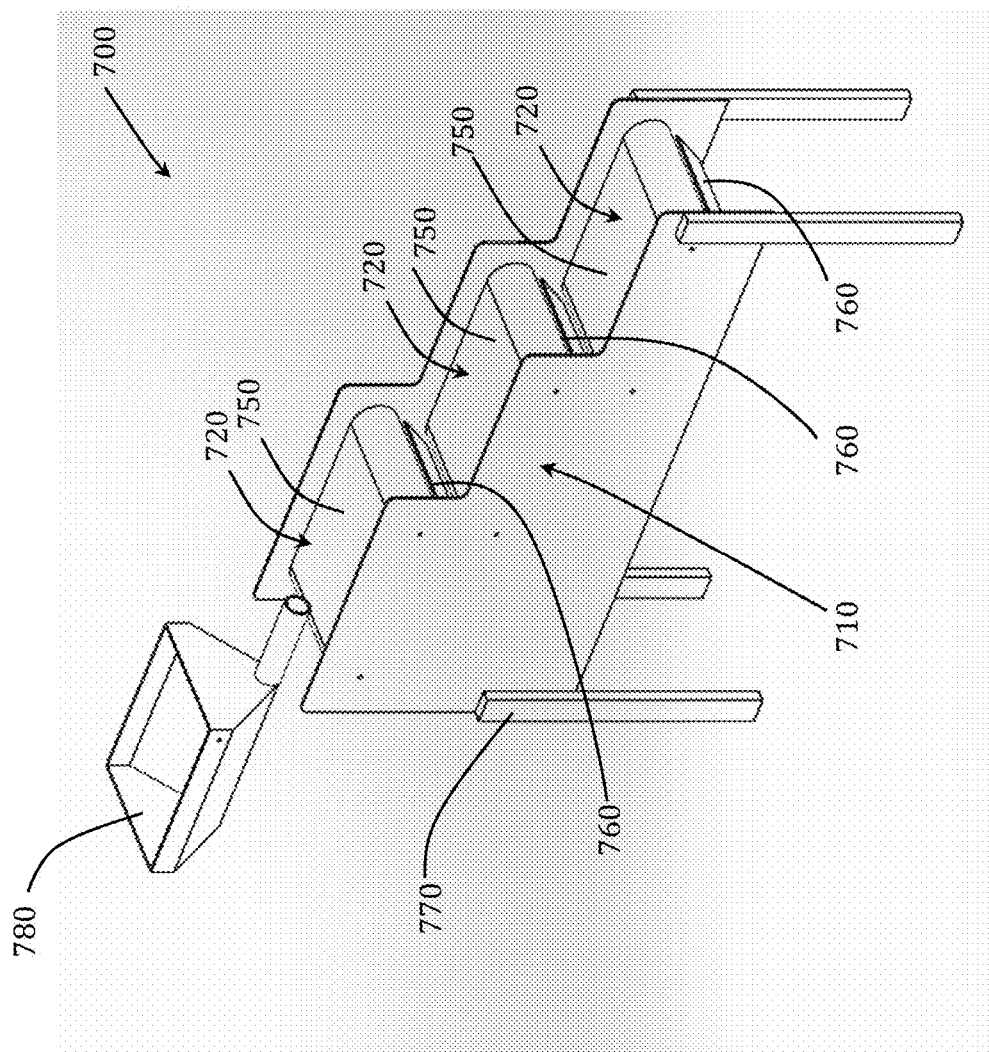
FIG. 8 is a perspective view of a representative insect sorting system according to an embodiment of the present disclosure.
Figure 9:
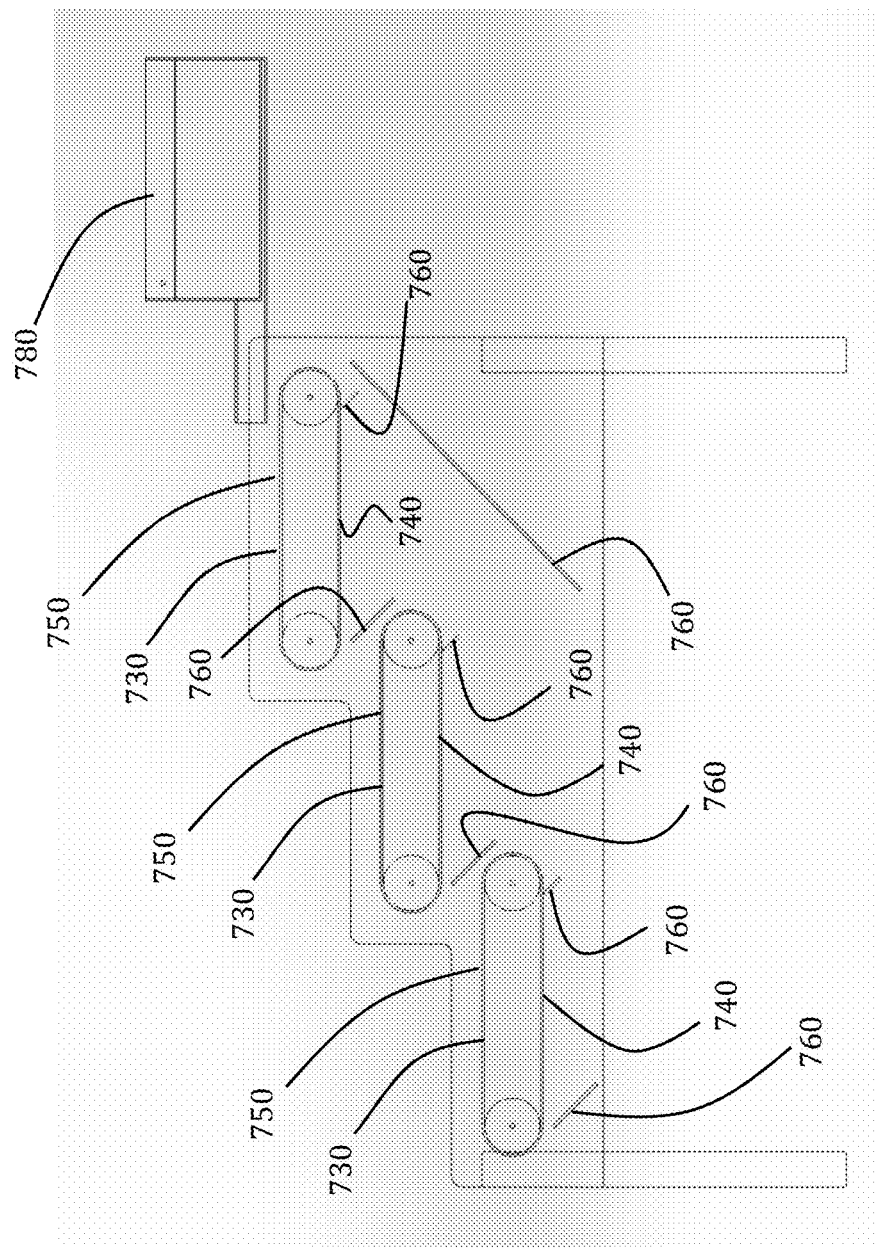
FIG. 9 is a side view of the insect sorting system of FIG. 8.

FIGS. 8-9 illustrate an insect sorting system 700 that is similar in some respects to the systems 100, 400 of FIGS. 1-7. As such, the following system 700 may have any feature of the systems 100, 400 of FIGS. 1-7 except where expressly stated otherwise and vice versa. The system 700 of FIGS. 8-9 includes a conveyor stage 710 having three tiered continuous loops 720, each continuous loop 720 forming an upper section 730 and a lower section 740, and each successive continuous loop 720 being located gravitationally below the preceding continuous loop 720. Each continuous loop 720 has a grasping surface 750 facing outwardly therefrom, and one or more diverters 760 positioned adjacent to the lower section 740. The system 700 is at least partially supported upon a frame 770 and includes an optional hopper 780 and optional collectors (not shown) as well as one or more drive systems (not shown) to drive the grasping surfaces 750 past the diverters 760.

Each continuous loop 720 has a flexible belt, chain, or similar structure that enables reliable and continuous movement. The grasping surface 750 may be applied to such belt, chain, or similar structure (as with adhesive, fasteners, or similar means). Or, the grasping surface 750 may substantially form the belt, chain, or similar structure of the continuous loop 720. Each diverter 760 may include a scraper, a fixed brush, a rotating brush, a wiper, a straight edge, an air curtain, or a liquid curtain that is positioned approximately transverse to the direction of movement of the grasping surface. Each continuous loop 720 may utilize more than one diverter type to improve sorting efficiency. To improve sorting efficiency for different insect supplies that include insects having different species, ages, or other characteristics, each successive grasping surface 750 may have different surface characteristics than the preceding grasping surface 750.

In use, an insect supply is provided on the gravitationally highest grasping surface 750 (e.g., from the hopper 780). The drive system rotates the continuous loop 720 in a forward direction (i.e., toward the next successive continuous loop 720). Active insects grasp the outwardly-facing grasping surface 750, and are transported to the lower section 740 of the continuous loop 720 and past the one or more diverters 760, which remove the active insects from the grasping surface 750 and cause them to fall into one or more collectors (via an optional chute). The inactive insects do not grasp the grasping surface 750, and therefore fall off the end of each continuous loop 720 and onto the next successive continuous loop 720, and ultimately into a collector. In this manner, the active insects are sorted from the inactive insects.

Figure 10:
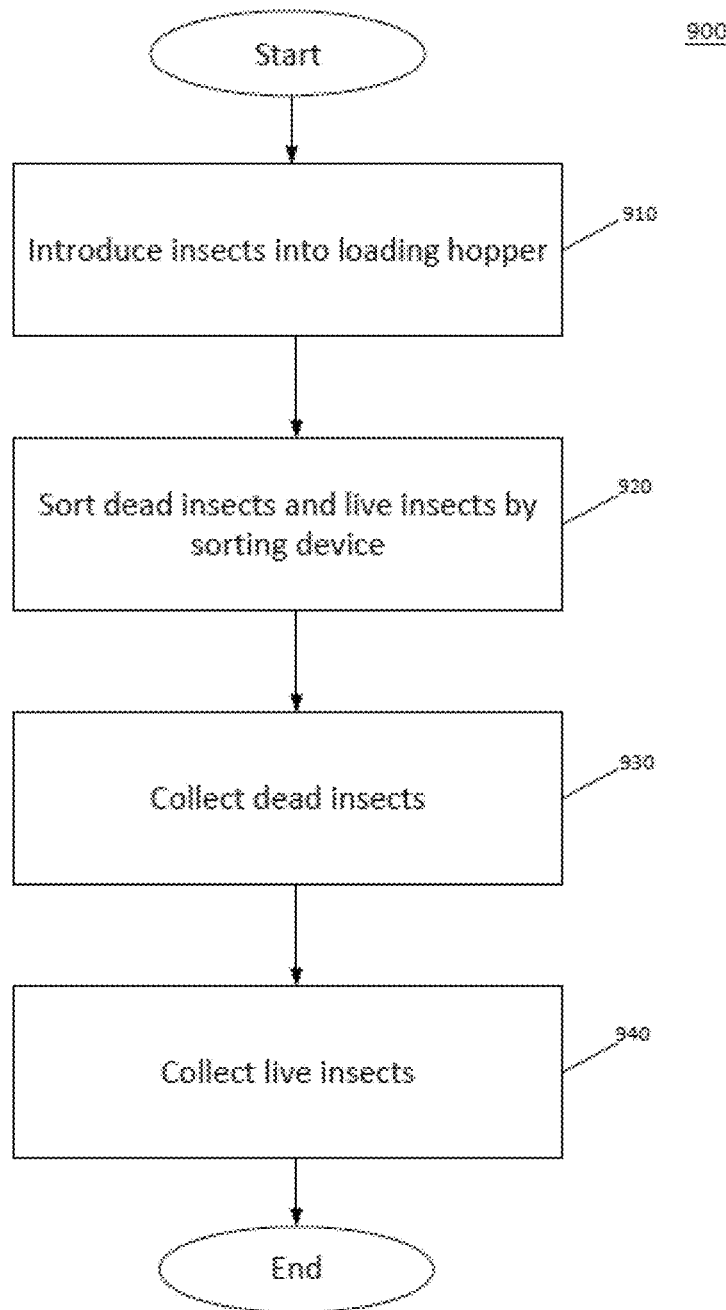
FIG. 10 is a diagram illustrating a method of sorting insects according to an embodiment of the present disclosure.

FIG. 10 illustrates a method 900 for sorting insects. At step 910, an insect supply is introduced into a loading hopper. At step 920, an active portion of the insect supply is sorted from an inactive portion of the insect supply by an insect sorting system, e.g., a conveyor stage. At step 930, the inactive portion of the insect supply is then collected (e.g., in a first collector). At step 940, the active portion of the insect supply is collected (e.g., in a second collector). In some embodiments, the active portion of the insect supply may be collected before or simultaneous with the inactive portion, rather than after.

Figure 11:
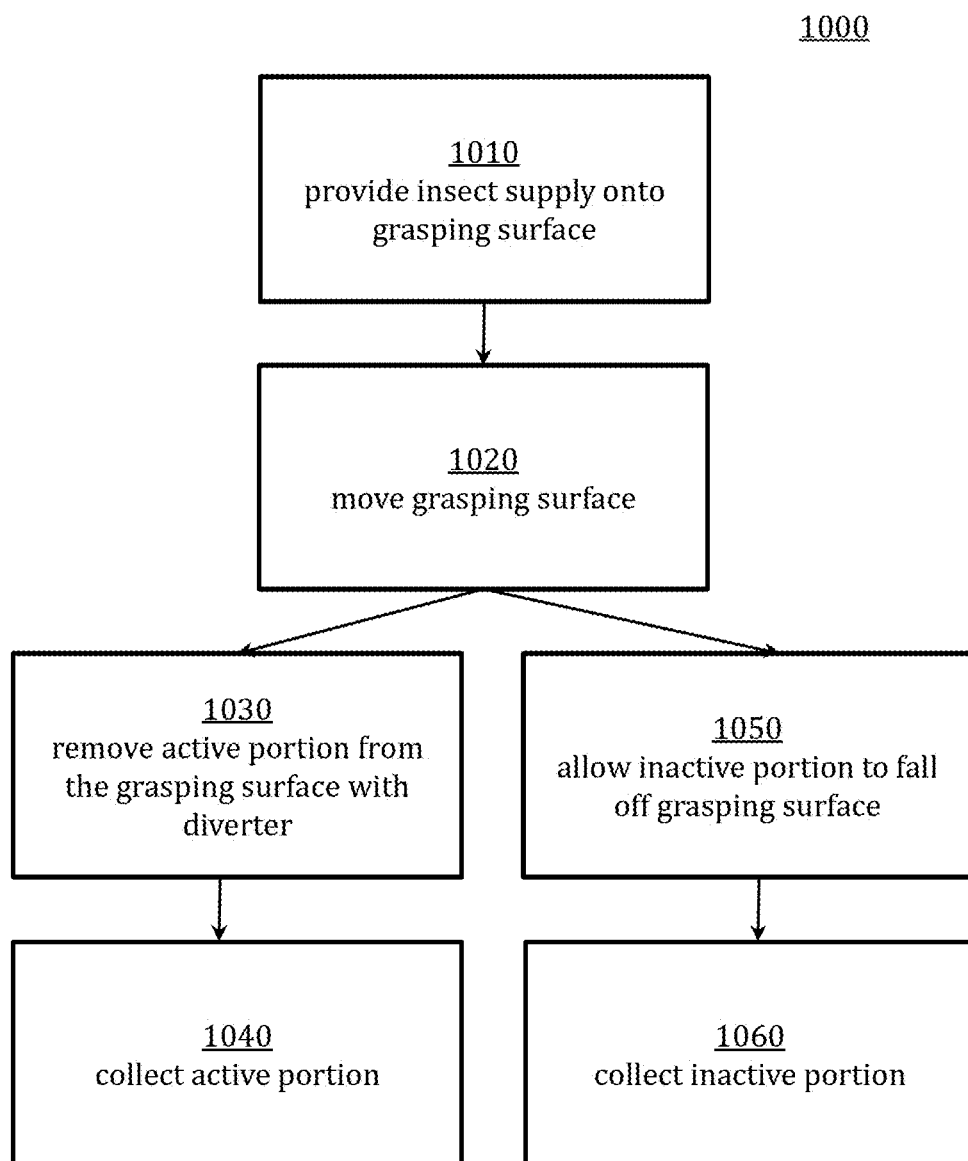
FIG. 11 is a diagram illustrating another method of sorting insects according to an embodiment of the present disclosure.

FIG. 11 illustrates another method 1000 for sorting insects. At step 1010, an insect supply is provided onto a grasping surface as described above with respect to any of the embodiments of FIGS. 1-8. Subsequently, an active portion of the insect supply may begin to grasp the grasping surface. At step 1020, the grasping surface is moved, e.g., with a drive unit. At step 1030, the active portion of the insect supply is separated from an inactive portion of the insect supply by moving the grasping surface past a diverter as described above. For example, the active portion may be separated from the inactive portion by rotating a cylindrical grasping surface past one or more scraper-type diverters at a rate of about 0.5 cm/s to about 100 cm/s. At step 1040, the active portion may be collected by falling into a first collector. At steps 1050, 1060, the inactive portion may be allowed to fall off the grasping surface, e.g., into a second collector.

In summary, the foregoing embodiments are advantageous over a conventional insect sorting systems, devices, and methods, such as manually sorting insects by humans, for at least two different reasons: efficiency and cost. These insect sorting systems can quickly sort active insects (e.g., live insects such as larvae) without significant labor costs. Further, in a large scale insect farming environment, sorting live insects from active insects from inactive insects (e.g., dead or non-larval insects) is crucial to harvesting proper-staged insects and to maintaining the quality of the freshly harvested insects.

The subject matter disclosed herein is described with specificity to meet statutory requirements, but is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

All references, including publications, patent applications, and patents, cited herein are hereby incorporated by reference to the same extent as if each reference were individually and specifically indicated to be incorporated by reference and/or were set forth in its entirety herein.

As used herein, the term "about" indicates the associated value can modified plus or minus 5% and still fall within the disclosed embodiment.

The use of the terms "a" and "an" and "the" and similar referents in the specification and in the following claims are to be construed to cover both the singular and the plural, unless otherwise indicated herein or clearly contradicted by context. The terms "having," "including," "containing" and similar referents in the specification and in the following claims are to be construed as open-ended terms (e.g., meaning "including, but not limited to,") unless otherwise noted. Recitation of ranges of values herein are merely intended to serve as a shorthand method of referring individually to each separate value inclusively falling within the range, unless otherwise indicated herein, and each separate value is incorporated into the specification as if it were individually recited herein. All methods described herein can be performed in any suitable order unless otherwise indicated herein or clearly contradicted by context. The use of any and all examples, or exemplary language (e.g., "such as") provided herein, is intended merely to better illuminate embodiments and does not pose a limitation to the scope of the disclosure unless otherwise claimed. No language in the specification should be construed as indicating any non-claimed element as essential to each embodiment of the present disclosure.

Different arrangements of the components depicted in the drawings or described above, as well as components and steps not shown or described are possible. Similarly, some features and sub-combinations are useful and may be employed without reference to other features and sub-combinations. Embodiments have been described for illustrative and not restrictive purposes, and alternative embodiments will become apparent to readers of this patent. Accordingly, the present subject matter is not limited to the embodiments described above or depicted in the drawings, and various embodiments and modifications can be made without departing from the scope of the claims below.

While illustrative embodiments have been illustrated and described, it will be appreciated that various changes can be made therein without departing from the spirit and scope of the invention.

The invention claimed is:

1. An insect sorting system, comprising:
a conveyor stage, comprising:
a drive unit;
a grasping surface movably coupled with the drive unit and having textured surface elements;
a diverter that is configured to remove insects from the grasping surface; and
a trough within an angled tube, at least part of the trough being positioned gravitationally below the diverter, wherein the diverter is contiguous with the trough.

2. The insect sorting system of claim 1, wherein the diverter is positioned within 5.0 mm from the grasping surface.

3. The insect sorting system of claim 1, wherein the conveyor stage is configured to move the grasping surface past the diverter at a rate that is between 0.5 cm per second and 100 cm per second.

4. The insect sorting system of claim 1, wherein the grasping surface is located within the angled tube.

5. The insect sorting system of claim 1, wherein the angled tube is substantially formed by the grasping surface.

6. The insect sorting system of claim 1, wherein the diverter is positioned external to the angled tube.

7. The insect sorting system of claim 1, wherein a longitudinal axis of the conveyor stage forms an angle that is between 5 degrees and 30 degrees relative to a horizontal surface.

8. The insect sorting system of any of claim 1, wherein the diverter is selected from the group consisting of: a fixed brush, a rotating brush, a wiper, a scraper, a straight edge, a gas curtain, and a liquid curtain.

9. The insect sorting system of claim 1, wherein the grasping surface comprises a mesh.

10. The insect sorting system of claim 1, further comprising a hopper having an outlet, at least a portion of the conveyor stage being located gravitationally below the outlet.

11. The insect sorting system of claim 1, further comprising a collector located gravitationally below the diverter.

\* \* \* \* \*